United States Patent [19]
Egedy et al.

[11] Patent Number: 6,034,281
[45] Date of Patent: Mar. 7, 2000

[54] PURIFICATION OF DIETHYLENE GLYCOL MONOETHYL ETHER

[75] Inventors: Charles R. Egedy, Baton Rouge; Christian C. Clause, Slaughter, both of La.

[73] Assignee: Ferro Corporation, Cleveland, Ohio

[21] Appl. No.: 09/198,879

[22] Filed: Nov. 24, 1998

[51] Int. Cl.$^7$ .................................................. C07L 43/11
[52] U.S. Cl. ............................................................ 568/621
[58] Field of Search ............................................. 568/621

[56] References Cited

U.S. PATENT DOCUMENTS

| | | | |
|---|---|---|---|
| 4,276,126 | 6/1981 | Saffer | 203/69 |
| 5,425,853 | 6/1995 | Berg | 203/57 |
| 5,507,878 | 4/1996 | Flaningam et al. | 134/42 |

FOREIGN PATENT DOCUMENTS

| | | |
|---|---|---|
| 2831210 | 5/1980 | Germany . |
| 089236 | 7/1980 | Japan . |

*Primary Examiner*—Paul J. Killos
*Attorney, Agent, or Firm*—Rankin, Hill, Porter & Clark LLP

[57] ABSTRACT

The present invention provides a method for purifying diethylene glycol monoethyl ether, which is commonly known as Carbitol™ or Ethyl Carbitol™. The method according to the present invention includes combining n-heptanol as an azeotrope-forming agent to crude diethylene glycol monoethyl ether which contains ethylene glycol as an impurity to form a mixture, subjecting the mixture to distillation whereby an overhead product comprising an azeotrope of ethylene glycol and n-heptanol and a bottoms product are produced, and recovering purified diethylene glycol monoethyl ether from the bottoms product. By practicing the method of the present invention, the ethylene gylcol content of diethylene glycol monoethyl ether can be reduced from thousands of parts per million to less than about twenty-five parts per million such that the purified diethylene glycol monoethyl ether is suitable for use as a solvent in pharmaceutical manufacturing applications.

11 Claims, No Drawings

PURIFICATION OF DIETHYLENE GLYCOL MONOETHYL ETHER

FIELD OF THE INVENTION

The present invention relates to a method for purifying diethylene glycol monoethyl ether, which is commonly known as Carbitol™ or Ethyl Carbitol™. More particularly, the present invention relates to a method for removing ethylene glycol from diethylene glycol monoethyl ether by azeotropic distillation using n-heptanol as an azeotrope forming agent.

BACKGROUND

Diethylene glycol monoethyl ether is used as a solvent in a wide variety of manufacturing processes. The commercial grade typically contains from about 1,000 parts per million (hereinafter "ppm") by weight to about 2,000 ppm by weight ethylene glycol as an impurity. The presence of this amount of ethylene glycol, which is toxic when ingested, renders the commercial grade of diethylene glycol monoethyl ether unusable as a solvent in pharmaceutical manufacturing applications. In order to be suitable for use in pharmaceutical manufacturing applications, the ethylene glycol content of diethylene glycol monoethyl ether must be reduced to less than about 25 ppm by weight.

Removing ethylene glycol, which has a boiling point of 197.2° C. (Hawley's Condensed Chemical Dictionary, 13th Ed., 1997), from diethylene glycol monoethyl ether using conventional distillation equipment is difficult and inefficient because diethylene glycol monoethyl ether has an overlapping boiling point range of 195–202° C. (Hawley's Condensed Chemical Dictionary, 13th Ed., 1997). Thus, the yield of pharmaceutical grade diethylene glycol monoethyl ether using conventional distillation equipment is quite low. A method which would permit the effective and economic removal of ethylene glycol from diethylene glycol monoethyl ether is therefore highly desired.

Azeotropic distillation is a well-known means of separating two compounds having boiling points in close proximity. In a typical azeotropic distillation, a third compound which forms an azeotrope with only one of the closely boiling components is added to form a mixture, the mixture is subjected to distillation, and the azeotrope is removed as an overhead product thereby effecting separation of the compounds having close boiling points. Ideally, the azeotrope-forming agent, which is sometimes referred to as an entrainer, is separated from the component with which it forms the azeotrope by conventionally known means, such as by phase separation, and returned to the distillation apparatus for reuse.

Each closely boiling binary system presents its own special problems so as to render past experience of little value and future results unpredictable. Thus, the selection of an azeotrope-forming agent is seldom a simple task. Not only must an azeotrope-forming agent form an azeotrope with only one of the closely boiling components having the proper volatility, the components of the azeotrope must also be capable of being easily separated in highly pure form for reuse in the process or for recovery as a final saleable, useful product. Moreover, the azeotrope-forming agent preferably should be relatively inexpensive, nontoxic, nonreactive, and noncorrosive.

SUMMARY OF THE INVENTION

The present invention is directed to a method for purifying diethylene glycol monoethyl ether by removing ethylene glycol through azeotropic distillation. The method according to the present invention comprises adding n-heptanol as an azeotrope-forming agent to crude diethylene glycol monoethyl ether which contains ethylene glycol as an impurity to form a mixture, subjecting the mixture to azeotropic distillation whereby an overhead product comprising an azeotrope of ethylene glycol and n-heptanol and a bottoms product are produced, and recovering purified diethylene glycol monoethyl ether from the bottoms product.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION

An azeotrope is a mixture of two or more compounds, the relative composition of which does not change upon distillation. Although compounds which form an azeotrope do not form a new substance, they behave like a single substance in that the vapor produced by partial evaporation has the same relative composition as the liquid mixture. Thus, compounds which form an azeotrope distill at a constant temperature without change in relative composition and cannot be separated by conventional distillation.

One of ordinary skill in the art cannot predict or expect azeotropic formation even among positional or constitutional isomers (i.e., butyl, isobutyl, sec-butyl, and tert-butyl). Moreover, compounds which are known to form an azeotrope in one binary system may not form a suitable azeotrope in another binary system. The unpredictability of azeotrope formation is well documented in U.S. Pat. Nos. 3,085,065; 4,157,976; 4,994,202; 5,064,560; and 5,507,878. Since azeotropism is an unpredictable phenomenon, each azeotropic combination must be separately discovered for each binary system.

After much experimentation, it has been found that ethylene glycol can be removed from crude diethylene glycol monoethyl ether by azeotropic distillation when n-heptanol is added thereto to form an azeotrope with ethylene glycol. It is reported that the n-heptanol/ethylene glycol azeotrope has a boiling point of about 174.1° C. and an ethylene glycol content of about 20%. See Lecat, Bull. Classe Sci. Acad. Roy. Belg. 29, 273 (1943).

Use of n-heptanol as an azeotrope forming agent in the ethylene glycol/diethylene glycol monoethyl ether binary system fills several important requirements. First, n-heptanol sufficiently enhances the volatility of ethylene glycol such that it can be efficiently removed from diethylene glycol monoethyl ether by azeotropic distillation. Second, n-heptanol has a boiling point (175° C.) which is sufficiently below that of diethylene glycol monoethyl ether (195–202° C.) such that purified diethylene glycol monoethyl ether can be efficiently recovered from the bottoms product by conventional distillation. Third, n-heptanol can be easily recovered for reuse by washing the overhead product with water and then recovering the n-heptanol from the organic phase by conventional distillation. And fourth, n-heptanol is relatively inexpensive, nontoxic, nonreactive, and noncorrosive.

The distillation equipment which can be used in practicing the present invention may be of any conventional type. However, it has been found that purification of diethylene glycol monoethyl ether according to the present invention can be accomplished very efficiently and economically using a packed column containing from about 30 to about 100 theoretical plates.

Reboiler temperatures used in the azeotropic distillation according to the method of the present invention are dependent in large part upon the operating pressures of the distillation equipment. In a preferred embodiment, the distillation equipment is operated at a pressure significantly below atmospheric pressure. Column pressure and reboiler temperature are not per se critical, and a range of column pressures and reboiler temperatures can be employed.

The amount of n-heptanol to be added to the crude diethylene glycol monoethyl ether will vary based upon the amount of ethylene glycol to be removed. For purification of commercial grade diethylene glycol monoethyl ether containing about 1,000 ppm to 2,000 ppm ethylene glycol as an impurity, the addition of approximately 15% to 20% n-heptanol by weight of diethylene glycol monoethyl ether is generally sufficient. More or less n-heptanol can be added to crude diethylene glycol monoethyl ether depending on the ethylene glycol content.

The method according to the present invention comprises adding n-heptanol as an azeotrope forming agent to crude diethylene glycol monoethyl ether to form a mixture. The mixture is then subjected to distillation whereby the azeotrope between n-heptanol and ethylene glycol is removed as an overhead product. After the ethylene glycol/n-heptanol azeotrope has been removed, the volume of matter remaining in the reboiler, which is sometimes referred to herein as the bottoms product, will comprise diethylene glycol monoethyl ether containing very little, preferably less than about 25 ppm, ethylene glycol. Purified diethylene glycol monoethyl ether can be recovered from the bottoms product by distillation. In a preferred embodiment, the reboiler temperature is successively increased allowing the purified diethylene glycol monoethyl ether to also be recovered as an overhead product. The n-heptanol used to form the azeotrope with ethylene glycol can be recovered from the overhead product by washing the overhead product with water, separating the organic phase from the aqueous phase, and then recovering purified n-heptanol from the organic phase by distillation.

The following examples are intended only to illustrate the invention and should not be construed as imposing limitations upon the claims:

EXAMPLE 1

1,245 grams of commercial grade diethylene glycol monoethyl ether were charged to a 5-L three neck round bottom flask equipped with a 36"×1" distillation column packed with ⅛"×1/16" stainless steel mesh packing, a mechanical stirrer, and a thermometer. The packing material is available as Pro-pack from Ace Glass, 1430 Northwest Boulevard, Vineland, N.J. and provides approximately 30 to 35 theoretical plates in this configuration. The system was brought to a pressure of about 50 mm Hg and the contents of the flask were heated to boil-up at about 126° C. Overhead reflux was obtained at 120° C., and a series of overhead cuts were taken until the purity of diethylene glycol monoethyl ether obtained overhead was 99.95+% and contained less than 100 ppm ethylene glycol. The purity of the material was established by gas chromatographic analysis by comparison to standards spiked with known quantities of ethylene glycol. A total of 313.8 grams of diethylene glycol monoethyl ether having a purity of 99.97% and containing less than 25 ppm ethylene glycol were recovered from the system, providing a yield of only 25.2% based upon the initial amount of diethylene glycol monoethyl ether charged to the pot.

EXAMPLE 2

1,245 grams of commercial grade diethylene glycol monoethyl ether and 210.7 grams n-heptanol (16.93% by weight) were charged to a 5-L three neck round bottom flask equipped with a 36"×1" distillation column packed with ⅛"×1/16" stainless steel mesh packing, a mechanical stirrer, and a thermometer. The system was brought to a pressure of about 50 mm Hg and the contents of the flask were heated to boil-up at about 126° C. Overhead reflux was obtained at 120° C., and a series of overhead cuts were taken until the purity of diethylene glycol monoethyl ether obtained overhead was 99.95+% and contained less than 100 ppm ethylene glycol. A total of 794.57 grams of diethylene glycol monoethyl ether having a purity of 99.97% and containing less than 25 ppm ethylene glycol were recovered from the system, providing a yield of 63.8% based upon the initial amount of diethylene glycol monoethyl ether charged to the pot.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method for purifying diethylene glycol monoethyl ether comprising:

combining n-heptanol with diethylene glycol monoethyl ether containing ethylene glycol to form a mixture, said n-heptanol comprising an azeotrope forming agent, subjecting said mixture to distillation whereby an overhead product is produced and a bottoms product is produced, said overhead product comprising an azeotrope of ethylene glycol and n-heptanol, and recovering diethylene glycol monoethyl ether from said bottoms product.

2. The method of claim 1 wherein said mixture is subjected to distillation at a pressure below atmospheric pressure.

3. The method of claim 1 wherein said overhead product is subjected to high rectification during distillation.

4. The method of claim 1 wherein the recovery of said diethylene glycol monoethyl ether from said bottoms product is accomplished by distillation.

5. The method of claim 1 further comprising:

washing said overhead product with water whereby an aqueous phase and an organic phase is formed; and recovering n-heptanol from said organic phase.

6. The method of claim 5 wherein the recovery of n-heptanol from said organic phase is accomplished by distillation.

7. The method of claim 5 further comprising recycling said n-heptanol recovered from said organic phase for use as said azeotrope-forming agent.

8. The method of claim 1 wherein the ethylene glycol content of the diethylene glycol monoethyl ether prior to forming the mixture with n-heptanol is more than about 1,000 ppm by weight.

9. The method of claim 1 wherein the ethylene glycol content of the diethylene glycol monoethyl ether recovered from said bottoms product is less than about 25 ppm by weight.

10. The method of claim 1 wherein the ethylene glycol content of the diethylene glycol monoethyl ether recovered from said bottoms product is less than about 10 ppm by weight.

11. The method of claim 1 wherein said mixture comprises from about 1 to about 30 percent by weight of said azeotrope-forming agent.

* * * * *